(12) United States Patent
Moulin et al.

(10) Patent No.: US 7,812,942 B2
(45) Date of Patent: Oct. 12, 2010

(54) METHOD FOR DETECTING SURFACE DEFECTS ON A SUBSTRATE AND DEVICE USING SAID METHOD

(75) Inventors: Cécile Moulin, Seyssinet Pariset (FR); Sophie Moritz, Grenoble (FR); Philippe Gastaldo, Pontcharra (FR); François Berger, Saint Chef (FR); Jean-Luc Delcarri, Saint Ismier (FR); Patrice Belin, Auxerre (FR); Christophe Maleville, La Terrasse (FR)

(73) Assignees: S.O.I. Tec Silicon on Insulator Technologies, Bernin (FR); Altatech Semiconductor, Montbonnot Saint Martin (FR)

( * ) Notice: Subject to any disclaimer, the term of this patent is extended or adjusted under 35 U.S.C. 154(b) by 30 days.

(21) Appl. No.: 12/057,367

(22) Filed: Mar. 27, 2008

(65) Prior Publication Data

US 2009/0051930 A1 Feb. 26, 2009

(30) Foreign Application Priority Data

Mar. 28, 2007 (FR) .................................. 07 54088

(51) Int. Cl.
*G01N 21/00* (2006.01)
(52) U.S. Cl. ............... 356/237.2; 356/237.4; 356/237.5
(58) Field of Classification Search .... 356/237.1–241.6
See application file for complete search history.

(56) References Cited

U.S. PATENT DOCUMENTS

| | | | | |
|---|---|---|---|---|
| 4,030,830 A | * | 6/1977 | Holly | .......................... 356/489 |
| 4,696,572 A | * | 9/1987 | Ono | ........................... 356/458 |
| 4,844,616 A | * | 7/1989 | Kulkarni et al. | ............. 356/495 |
| 5,633,721 A | * | 5/1997 | Mizutani | .................... 356/401 |
| 6,731,391 B1 | | 5/2004 | Kao et al. | |
| 6,750,899 B1 | | 6/2004 | Fishbaine et al. | |
| 7,372,062 B2 | * | 5/2008 | Tanaka | .................. 250/559.45 |

(Continued)

FOREIGN PATENT DOCUMENTS

DE 103 44 051 4/2005

(Continued)

OTHER PUBLICATIONS

International Search Report of PCT/EP2008/053663, mailed May 21, 2008, S.O.I.TEC Silicon on Insulator Technologies.

(Continued)

*Primary Examiner*—Gregory J Toatley, Jr.
*Assistant Examiner*—Jarreas C Underwood
(74) *Attorney, Agent, or Firm*—Adeli & Tollen LLP (57) ABSTRACT

A method for detecting surface defects, such as slip line type defects, on a substrate designed to be used in electronics, optoelectronics or analogue, including projection of a pattern of light fringes and dark bands onto the substrate, relative displacement of the substrate relative to the pattern, acquisition of a sequence of at least three images of the pattern reflected by the substrate to a sensor, the images corresponding to displacement of the fringes of the pattern, determination of the gradient of the surface of the substrate using displacements of fringes of the pattern, and determination of the presence of a surface defect on the substrate using variations in the gradient of the surface of the substrate. Another embodiment comprises a device using said method.

19 Claims, 4 Drawing Sheets

U.S. PATENT DOCUMENTS

| | | | |
|---|---|---|---|
| 7,570,366 B2 * | 8/2009 | LeBlanc | 356/497 |
| 2001/0033386 A1 | 10/2001 | Kranz et al. | |
| 2006/0050284 A1 | 3/2006 | Bertin-Mourot et al. | |

FOREIGN PATENT DOCUMENTS

| | | |
|---|---|---|
| EP | 0 798 773 | 10/1997 |
| EP | 0 924 494 | 6/1999 |
| FR | 2 817 042 | 5/2002 |
| JP | 60122358 | 6/1985 |
| JP | 3150859 | 6/1991 |
| JP | 03150859 | 6/1991 |
| JP | 04 042 945 | 2/1992 |
| JP | 8068619 | 3/1996 |
| JP | 08068619 | 3/1996 |
| JP | 11 118730 | 4/1999 |
| JP | 11118730 | 4/1999 |
| JP | 11 257930 | 9/1999 |
| JP | 11257930 | 9/1999 |
| JP | 2001 124538 | 5/2001 |
| JP | 2001124538 | 5/2001 |
| WO | WO 2008/116917 | 10/2008 |

OTHER PUBLICATIONS

Written Opinion of PCT/EP2008/053663, mailed May 21, 2008, S.O.I.TEC Silicon on Insulator Technologies.

Surrel, Yves, "Moiré et déflectométrie", Atelier Photomécanique, Jun. 2004, pp. 1-41, Saint-Étienne, France.

Surrel, Yves, "Design of algorithms for phase measurements by the use of phase stepping", Jan. 1996, Applied Optics, vol. 35, No. 1.

Surrel, Yves.: "Contrôle de Défauts D'Aspect et de Qualité de Surface—La solution par la Déflectométrie," Contrôles-Essais-Mesures, Apr. 2006, pp. 11-14 (including English abstract).

Zani, M. L.: "Contrôle Optique—Une Autre Maniére de "Voir" les Défauts de Surface," Mesures, Mar. 2001, pp. 73-77, vol. 733 (including English abstract).

Surrel, Yves.: "Checking Visual Defects and Surface Finish Quality—The solution with deflectometry," Contrôles-Essais-Mesures, Apr. 2006, pp. 11-14 (English translation of item #1 in the 1449 filed Apr. 12, 2010).

Surrel, Yves.: Optique C1-18851 Images optiques; mesures 2D et 3D Polycopié de cours-2003/2004, Conservatoire National des Arts et Métiers, Oct. 8, 2003, pp. 1-171.

Surrel, Yves,: "Chapter 9: Slope measurements: deflectometry," Optique C1-18851 Images optiques; mesures 2D et 3D Polycopié de cours-2003/2004, Conservatoire National des Arts et Métiers, Oct. 2003, pp. 101-108 (English translation of item #2 above).

Zani, M. L.: "Optical Control—Another Way to "See" Surface Defects," Mesures, Mar. 2001, pp. 73-77, vol. 733 (English translation of item #2 in the 1449 filed Apr. 12, 2010).

* cited by examiner

METHOD FOR DETECTING SURFACE DEFECTS ON A SUBSTRATE AND DEVICE USING SAID METHOD

FIELD OF THE INVENTION

This invention relates to a method for detecting surface defects on a substrate and a device using said method, particularly adapted for detecting and positioning surface defects in a semiconducting substrate, particularly crystalline microdefects in a mono-crystalline substrate.

BACKGROUND OF THE INVENTION

It is well known that surface defects appear during manufacturing of semiconducting substrates such as SOI (Silicon On Insulator) substrates intended specifically for micro-electronic, optoelectronic application, etc.

Said substrates are usually obtained by Smart-Cut™ and by a succession of heat treatments.

During these heat treatments, the substrate is subjected to temperature gradients and a plastic deformation that causes the appearance of surface defects called Slip lines on the active layer that reduce the substrate quality.

SOI substrates are held in place by supports during heat treatments, for example annular supports or supports with three or four bearing points, etc. During high temperature heat treatment steps, for example at a temperature exceeding 1000° C., the retaining support exerts high forces on the substrate and particularly shear stresses. These forces can deform the substrate and thus cause the formation of fracture planes in which the crystalline structure is offset by sliding after fracture, which can be observed in the form of corresponding slip lines. The shift amplitude may be of the order of one nanometer and thus generate steps of the same dimension on the surface. The fracture can cross through a part of the thickness of the substrate, and can sometimes cross through the substrate from its back face to its front face.

For example, high quality SOI type substrates require heat treatments at a temperature of 1100° C. or even more than 1200° C., causing the formation of slip lines, particularly close to contact zones between the substrate and the support holding the substrate in position during heat treatments.

Thus, an annular support typically shows up slip lines around the periphery of the substrate, while a support with three bearing points will make them appear in substrate bearing zones arranged facing the bearing points. The slip lines will deteriorate the quality of the monocrystalline silicon on insulator layer and consequently electronic components that are made later.

Such defects are not observed only on SOI type heterostructures, they also occur on other types of substrates, for example homogenous monocrystalline silicon substrates.

In order to maintain a good quality of marketed substrates, the usual practice is to examine the surface of these substrates to determine any slip lines that occur during manufacturing.

Fast and reliable detection of all slip lines using a single detection technique is found to be very difficult.

If several techniques commonly used in industry are used and the results are compared, it can be seen that there is no technique capable of identifying all slip lines and in particular slip lines that occur at the periphery of the substrate. Techniques based on detection of beams of reflected and/or scattered light at the surface of the substrate cannot be used around the edge of the substrate where the wafer has a rounded edge such that light cannot be collected and therefore the measurement cannot be made. Therefore the substrate is not analysed over several millimetres around its periphery.

Therefore, an attempt is made to find a detection tool capable of identifying all slip lines and other types of defects that can be detected by optical methods such as holes present in the surface, etc., in a single measurement.

There are powerful and complex laboratory devices that admittedly are capable of detecting practically all defects that can be detected optically, such as slip lines or holes present at the surface, etc.

However, these devices are very expensive and substrates can only be analyzed at a rate of about 7 substrates per hour.

A rate of 50 or even 100 substrates per hour would be necessary to be compatible with industrial production.

Most methods for the detection of slip lines on such substrates consist of projecting polarized coherent light emitted by a laser source onto the substrate, and using a photo-detector to detect light reflected by the substrate. When the incident beam is reflected on the surface of the substrate, light is scattered by the defects. The photo detector detects and quantifies this light scattered in this way.

Such methods are described for example in Japanese patents JP4042945 and JP60122358.

These methods have the disadvantage that they require a particularly long development time and their efficiency is not good. These methods are incapable of detecting low amplitude slip lines. In particular, these methods are incapable of detecting slip lines present on the edges of the substrate (the rounded edges make it impossible to satisfactorily collect reflected light), although slip lines are particularly frequent at edges.

Japanese patent JP3150859 also describes a method for detection of slip lines in a semiconducting substrate in which said substrate is placed under a differential interference microscope provided with a television camera connected to a converter. Said converter transforms the video signal from the camera into the form of an electrical current that is compared with a limiting defect detection current. The substrate is displaced along at least two directions orthogonal to the microscope centre line, so as to check the entire substrate surface.

This method has the disadvantage firstly that it can only be used to detect large slip lines, and secondly, that the processing time for a substrate according to this method is long and results in a limited supply rate of analysed substrates.

Japanese patent application JP 2001/124538 discloses a method and a device for detecting defect which occurs in the surface of a semiconductor wafer, such as slip lines. The method includes a step of projecting a pattern composed of an alternation of light fringes and dark bands on the substrate, so as to generate fringes reflected by the surface of the substrate. Subsequently, images of the pattern reflected by the substrate are captured by a CCD sensor and defects are visually detected on a display screen.

This method presents the disadvantage to be inefficient to detect small defects and to be prone to human error.

Prior art US 2001/0033386 discloses an optical system for detecting surface defects on an object including a step of projecting a pattern composed of an alternation of light fringes and dark bands on the substrate, so as to generate fringes reflected by the surface of the object, a step of relative displacement of the pattern and the object, a step of acquisition of a sequence of three images of the pattern reflected by the object, and a step of determination of the height as a function of the imaging according to U.S. Pat. No. 6,750,899. The height is determined for each pixel of the images in function of the variation of the relative phase of the fringes.

This method presents the disadvantage to be inefficient to detect small defects too.

Moreover, not all these methods can efficiently detect so-called non-transferred zones that can occur during a manufacturing process comprising a step to transfer a layer and then a step to detach the layer using SmartCut™ process. These ZNT zones are well known to those skilled in the art and correspond to regions in which molecular bonding is not as effective as the detachment mechanism, such that the layer is not transferred in these regions. ZNT zones at the edge of the substrate are not always detected, particularly in a zone in which measurements cannot be made due to the rounded edge of the substrate. It is also found that above a given size, these techniques are not very effective at detecting ZNT zones.

SUMMARY OF THE INVENTION

Therefore one of the purposes of this invention is to overcome all these disadvantages by proposing a technique for the detection of surface defects in a semiconducting substrate and a device making use of said simple design inexpensive method, and providing a fast means of detecting very small slip lines within less than 30 seconds.

To achieve this and in accordance with the invention, it is proposed to use a method of detecting surface defects such as slip lines, on a substrate designed to be used in electronics, optoelectronics or analogue; said method is remarkable in that it comprises at least the following steps:

- projection of a pattern composed of an alternation of light fringes and dark bands onto a substrate, so as to generate fringes reflected by the substrate surface,
- relative displacement of the pattern and the substrate along at least one direction, so as to displace the fringes of the pattern on the substrate,
- acquisition of a sequence of at least three images of the pattern reflected by the substrate by a sensor, the images corresponding to displacement of the fringes of the pattern,
- determination of the gradient of the surface of the substrate using displacements of fringes of the pattern, and
- determination of the presence of a surface defect on the substrate using variations in the gradient of the surface of the substrate.

Preferably, fringes of the pattern are parallel to each other and extend parallel to a first principal crystalline axis of the substrate and/or parallel to a second principal crystalline axis of the substrate.

Advantageously, a first sequence of images is acquired by projecting a pattern, the fringes of which are parallel to each other and extend parallel to the first principal crystalline axis of the substrate, said fringes being displaced along a direction perpendicular to the orientation of the fringes, and a second sequence of images is acquired by projecting a pattern for which the fringes are parallel and extend parallel to the second principal crystalline axis of the substrate, said fringes being displaced along a direction perpendicular to the orientation of the fringes.

Accessorily, the method according to the invention comprises a step to determine the position in space of defects determined from variations in the gradient of the substrate surface.

The position in space of the defects is determined by determining the points on the surface of the substrate with a radius of curvature greater than or equal to a given threshold value and/or with a spatial distribution statistically different from the average for the substrate.

This position in space of defects is determined using a reference point on the substrate.

To achieve this, the substrate consists of a flat disk comprising a radial notch around its periphery, forming the reference point.

Furthermore, the method according to the invention advantageously includes a step to determine the nature of the detected surface defects.

The nature of surface defects is determined by determining the amplitude and/or the length and/or shape and/or orientation of each detected surface defect.

Furthermore, the pattern and/or the substrate is moved along two orthogonal directions.

Another purpose of the invention relates to a device for the detection of surface defects such as slip line type defects, on a substrate designed to be used in electronics, optoelectronics or analogue; said device is remarkable in that it comprises means of projecting a pattern on said substrate composed of an alternation of continuous light fringes and dark bands, means of introducing relative displacement of the pattern and the substrate along at least one direction, at least one sensor capable of recording displacements of fringes reflected by the substrate, means of determining the gradient of the surface of the substrate using displacements of pattern fringes, and means of determining the presence of a surface defect on the substrate using variations in the gradient of the substrate surface.

Said means of projecting the pattern consist of a screen on which an image is displayed comprising a sequence of light fringes and dark bands.

Furthermore, said means of creating a relative displacement of the pattern and the substrate consist of an algorithm for processing the video signal transmitted to the screen so as to offset the light fringes and dark bands, the offset being between half a pixel and several pixels, at regular time intervals or irregular time intervals, the screen, substrate and the sensor being fixed.

Said sensor preferably consists of a digital camera comprising a CCD sensor.

Said means of determining the gradient and/or curvature of the substrate surface consist of an algorithm capable of calculating the phase offset of pattern fringes at each point on the surface of the substrate, using the signal transmitted by the sensor.

Said means of determining the presence of a surface defect consist of a second algorithm capable of calculating variations in the gradient and/or curvature at each point on the surface of the substrate using phase offsets calculated by the first algorithm.

Accessorily, the device according to the invention comprises means of determining the position in space of defects on the substrate surface.

Said means of determining the position in space of defects consist of an algorithm capable of calculating the abscissa and the ordinate of each point on the surface of said substrate with a radius of curvature greater than or equal to a determined threshold value and/or with a spatial distribution statistically different from the average of the substrate, relative to a reference point on the substrate.

In order to prevent any deposition of dust on the substrate, the device advantageously comprises means of generating a laminar flow of a fluid parallel to the surface of the substrate and/or means of supporting said substrate vertically.

BRIEF DESCRIPTION OF THE DRAWINGS

Other advantages and characteristics will become clearer after reading the following description given as a non-limitative example of a method for detecting surface defects on a substrate and the device making use of said method according to the invention, with reference to the attached drawings on which.

DETAILED DESCRIPTION OF THE INVENTION

Figure 1:
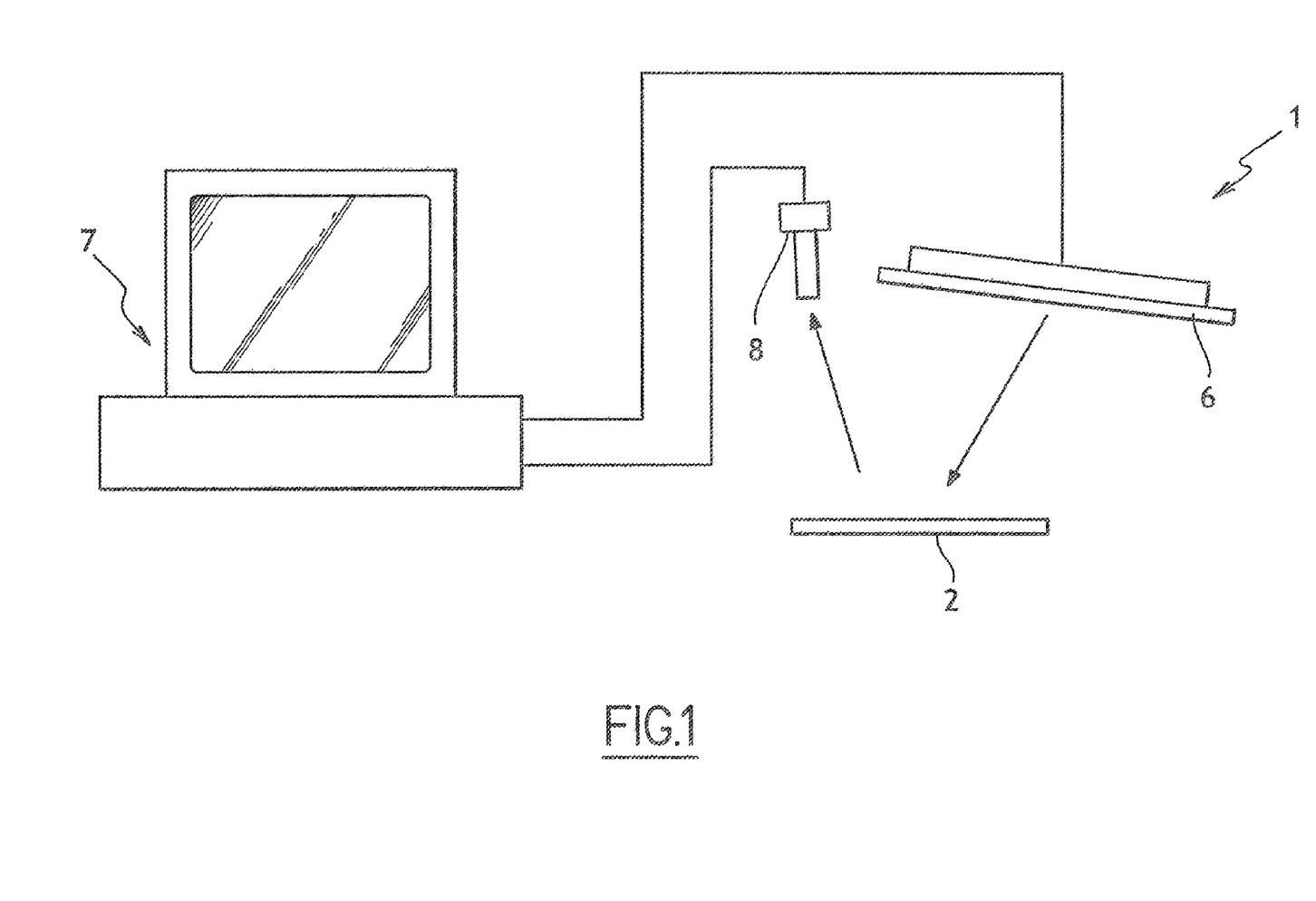
FIG. 1 is a diagrammatic view of the device for detection of surface defects in a substrate according to the invention.
Figure 2:
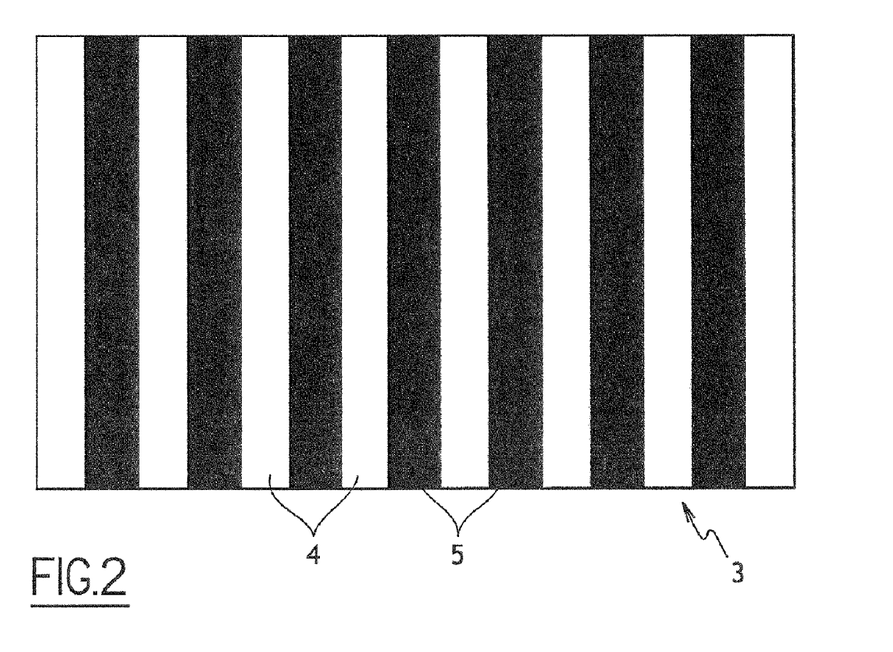
FIG. 2 is a diagrammatic representation of the pattern for the device according to the invention.

With reference to FIGS. 1 and 2, the device according to the invention comprises means of projecting 1 a pattern 3 composed of an alternation of fringes 4 of continuous light and dark bands 5, onto a substrate 2, said pattern 3 being shown in FIG. 2.

The substrate 2 is positioned on an annular type support not shown in the figures, or of the type consisting of three or four bearing points for example for a substrate with a diameter of 300 mm.

In this special example embodiment of the invention, it can be seen that the light fringes 4 and the dark bands 5 are approximately equal in width; however, it is quiet obvious that the light fringes 4 and the dark bands 5 could have arbitrary corresponding width, without going outside the framework of the invention.

These projection means 1 are composed of a screen 6, for example such as a plasma or LCD (Liquid Crystal Display) screen, positioned above said substrate 2 close to the normal to said substrate 2, connected to means of emitting a visual signal, for example such as a computer 7, and receiving a visual signal comprising a sequence of light fringes 4 and dark bands 5.

Preferably, a 50 inch LCD screen will be used. The homogeneity of pixels on LCD screens is more suitable for the detection of slip lines than is possible with plasma screens. The distance between such a screen 6 and the substrate 2 with a diameter of 300 mm may for example be 60 cm.

The screen 6 may also be replaced by a projection screen onto which a pattern is projected with a projector. In all cases, the screen 6 is preferably arranged perpendicular to the optical axis to obtain a homogenous resolution on the entire substrate.

The pattern 3 corresponds to structured light in the plane of the screen 6.

Figure 6:
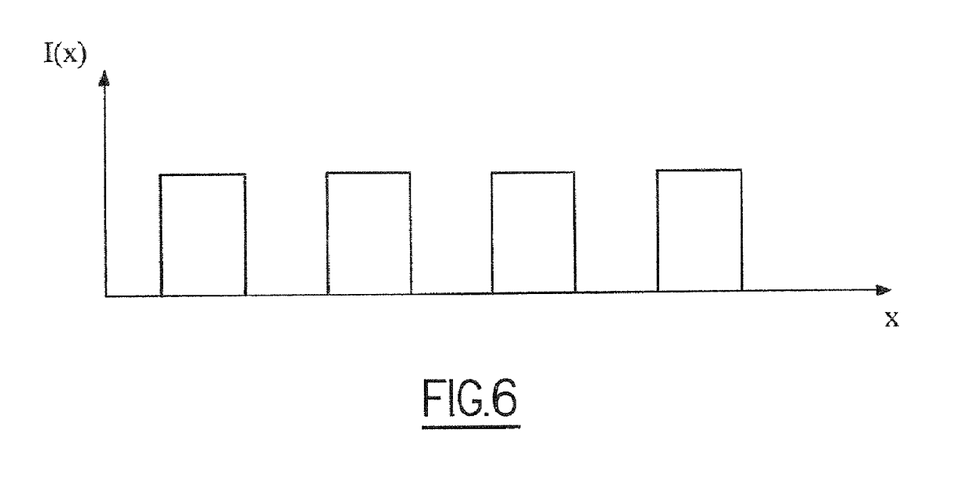
FIG. 6 is a graph showing a second variant of the distribution of light intensity in the pattern in the device according to the invention

In the example embodiment of the pattern 3 shown in FIG. 2, the distribution of light l(x) perpendicular to the fringes is globally notched (FIG. 6), in other words the intensity periodically changes between 0 and 100%.

Figure 4:
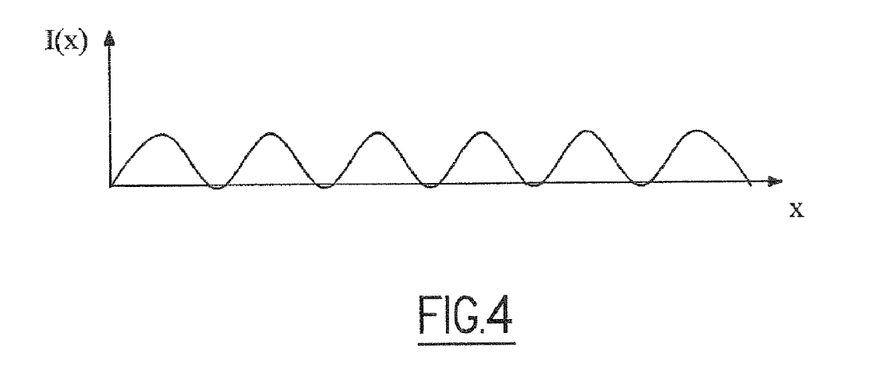
FIG. 4 is a graph showing the distribution of the intensity of light in the pattern represented in FIG. 2

Preferably, the pattern 3 is composed of parallel fringes, in which the distribution of the intensity l(x) perpendicular to the fringes is approximately sinusoidal (FIG. 4).

Figure 5:
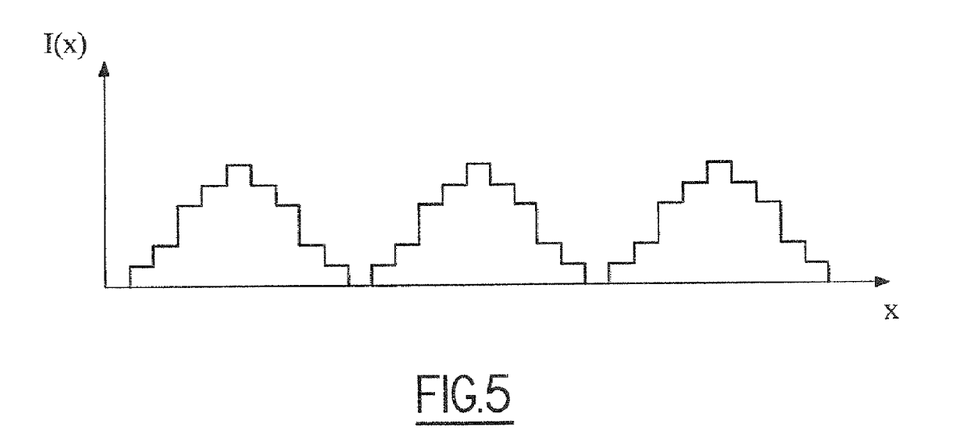
FIG. 5 is a graph representing a variant of the distribution of light intensity in the pattern of the device according to the invention.

It will be observed that when the period of this sine curve corresponds to about 10 pixels of the screen 6, the shape of the intensity distribution will be similar to that shown in FIG. 5.

In this example embodiment, it is preferable to use very thin fringes 4, for example corresponding to about ten pixels of the screen 6. With a screen 6 comprising 1000 pixels, this corresponds to about a hundred light fringes 4 reflected by the substrate 2.

It is obvious that said projection means 1 may be substituted by any other equivalent projection means capable of projecting a pattern 3 onto the substrate, the pattern being composed of an alternation of continuous light fringes 4 and dark bands 5. For example, these means could consist of a continuous and sinusoidal light source, i.e. non-coherent light, and a grid positioned between said light source and the substrate, or a coherent light source comprising two spherical waves providing sinusoidal fringes by interference between said waves.

The device also comprises means of relative displacement of the pattern 3 and the substrate 2 along at least one direction. In this particular embodiment, said displacement means advantageously consist of an algorithm for processing the video signal transmitted to the screen 6 so as to offset the light fringes 4 and dark bands 5 by a half, or one or several pixels at regular or irregular time intervals. The period of the fringes is not necessarily consistent with the pixels.

Preferably, the pattern 3 is displaced by a single pixel. Ten different images are thus recorded in the case of light fringes 4 with a sinusoidal intensity with a pitch of ten pixels on the screen.

Said pattern 3 may be displaced either step by step, in other words by a discrete displacement, or continuously along one or several directions.

With reference to FIG. 1, the device according to the invention comprises a sensor 8 particularly so as to record images of fringes 4 reflected by the substrate 2 and their displacements. This sensor 8 advantageously consists of a digital camera comprising a CCD (Charge-Coupled Device) type sensor with 11 million pixels. The camera is accommodated on the substrate 2 and not on the mirror image of the screen reflecting in the substrate 2. Such a camera can take an image in 500 ms, and then transfer the data to the computer in about 500 ms. Thus, in one second, a sufficiently precise image is obtained to be able to resolve slip lines using the method according to the invention. Therefore, the acquisition duration for a sequence of ten images lasts about ten seconds. It is thus possible to process two or even three substrates per minute, and thus more than a hundred substrates per hour.

This sensor 8 is connected to the computer 7 that receives information about the images reflected by the substrate 2, so as to process them.

It will be observed that as the resolution of the sensor 8 increases, the device according to the invention is capable of detecting increasingly small surface defects in the substrate.

Furthermore, it should be noted that in this particular embodiment, the screen 6, the substrate 2 and the sensor 8 are fixed such that the device does not generate any vibration, is not a source of contamination due to friction between parts, and it does not become unregulated. Moreover, the device is not very sensitive to vibrations.

This information is processed by means of determining the curvature of the surface of the substrate 2 using displacements of fringes 4 of the pattern 3.

These means of determining the curvature of the surface of the substrate 2 consist of an algorithm recorded on a support of the computer 7 and capable of calculating the phase offset of the fringes 4 of the pattern 3 at each point on the surface of the substrate 2 using the signal transmitted by the sensor 8 and then deducing the radius of curvature at said point on the surface of the substrate 2.

The device also comprises means of determining the presence of a surface defect on the substrate 2 using variations in the gradient of the substrate surface. These means of determining the presence of a surface defect consist of a second algorithm recorded on a medium in the computer 7 and capable of calculating values of the gradient at each point on the substrate surface using phase offsets calculated by the first algorithm.

Particularly advantageously, the device according to the invention comprises means of determining the position in space of defects on the surface of the substrate 2. Said means of determining the position of defects in space consist of an algorithm capable of calculating the abscissa and the ordinate of each point on the surface of said substrate 2 with a radius of curvature greater than or equal to a determined threshold value, relative to a reference point on the substrate 2.

According to one variant embodiment, said means of determining the position of defects in space could consist of an algorithm capable of calculating the abscissa and the ordinate of each point of the surface of said substrate 2 with a local gradient distribution statistically different from the gradient distribution in the rest of the substrate 2, relative to a reference point on the substrate 2.

Figure 3:
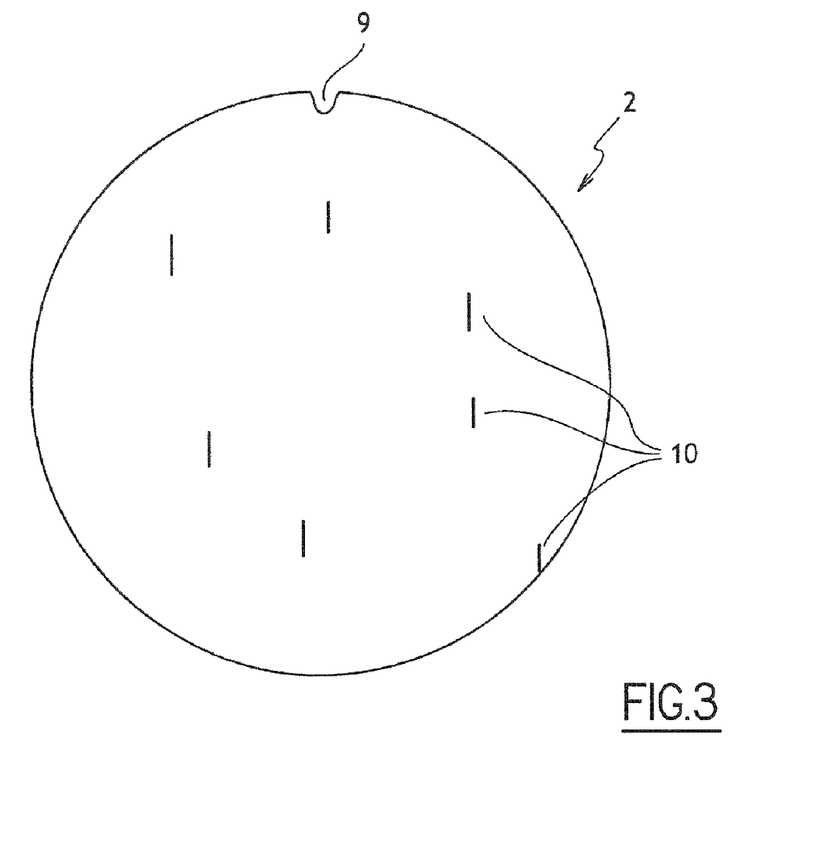
FIG. 3 is a top view of the substrate provided with a reference point for determination of the position of defects detected according to the invention.

In the example embodiment according to the invention as shown in FIG. 3, the substrate 2 consists of an SOI (Silicon On Insulator) type semiconducting substrate, in the form of a disk in which a radial notch 9 is formed at its periphery. This notch 9 acts as the reference point for an orthogonal coordinate system in which defects 10 detected at the surface of said substrate 2 can be located.

Accessorily, the device according to the invention comprises means of determining the nature of surface defects consisting of an algorithm recorded on a medium of the computer 7 and capable of calculating the amplitude and/or the length and/or shape and/or orientation of each detected surface defect 10, and then comparing these values with the values in a database.

Thus, the device can be used to detect and make a distinction between several types of surface defects, and particularly micro-defects for example crystalline defects such as slip lines at the periphery of the substrate or impacts of the support in zones at mid-distance between the centre and the edge of the substrate, the dimensions of which are of the order of several hundred micrometers for the length and the order of one nanometer for the depth. The device is also capable of detecting so-called non-transferred zones (ZNT) appearing during a manufacturing process consisting of a step to transfer a layer and then a detachment step using the SmartCut™ process.

In order to limit the deposition of dust on the substrate 2 and gravitational constraints that could cause deformation of the substrate 2 and that can modify detection of defects 10, said substrate 2 may advantageously be positioned vertically by any appropriate means well known to those skilled in the art.

Furthermore, the device according to the invention can advantageously include means of generating a preferably laminar flow of a fluid to minimize contamination of the substrate by dust, the substrate 2 preferably extending along the flow or close to and parallel to this flow.

We will now explain operation of the device according to the invention with reference to FIGS. 1 to 4.

A pattern 3, composed of fringes 4 for which the light intensity has a sinusoidal distribution along the axis perpendicular to the fringes (FIG. 4) is projected onto the substrate 2 in a step 100 (FIG. 7), so as to generate fringes reflected by the surface of said substrate.

The intensity of the image reflected by the substrate can be written in the following form:

$$I=I_0(1+A_o\cos(\phi+x))$$

where $I_0$, $A_0$, $\phi$ and x are unknowns and represent the average intensity of the image reflected by the substrate 2, the contrast of the fringes 4, the phase angle and a spatial coordinate of a first predetermined direction, respectively.

Figure 7:
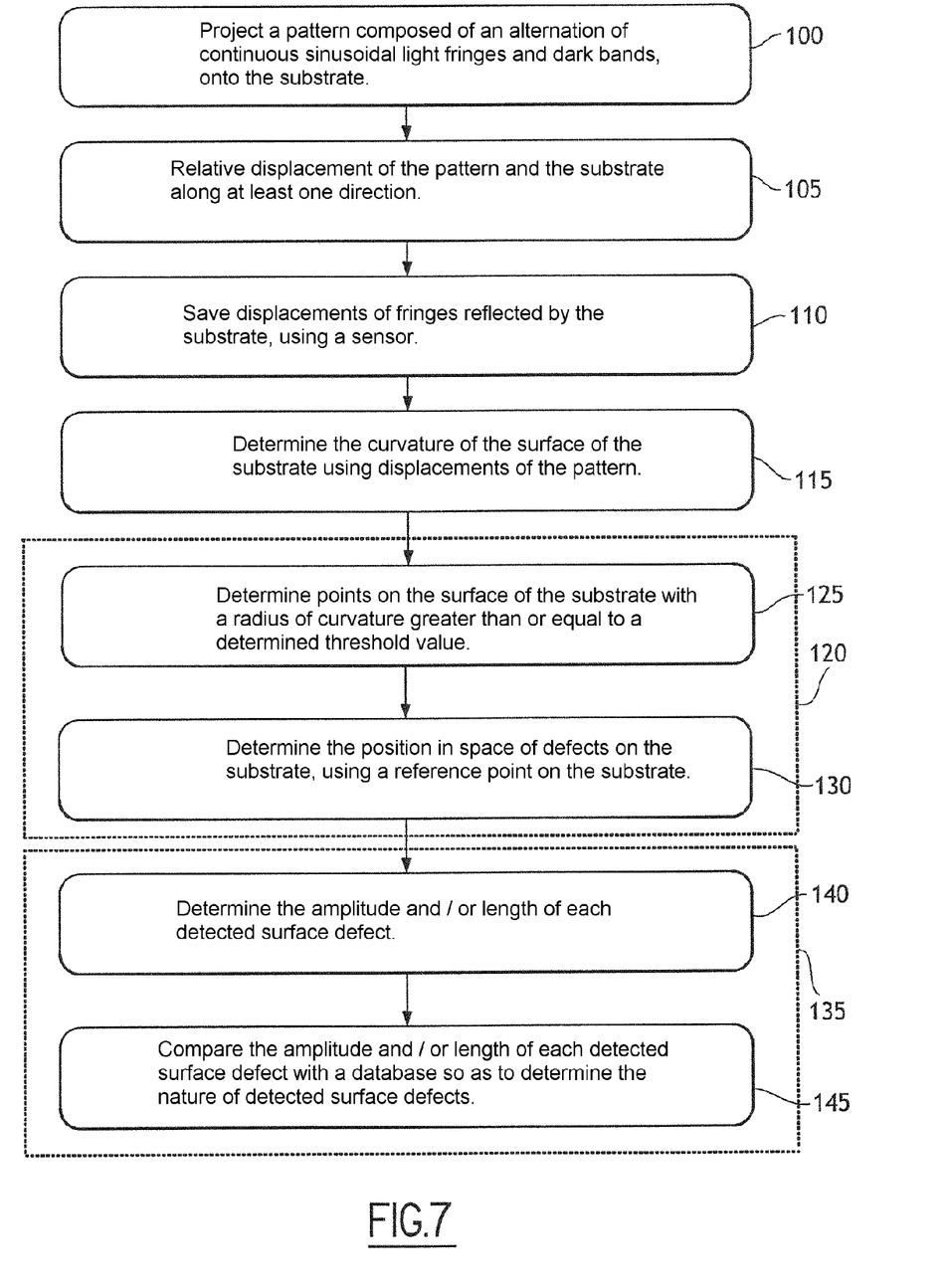
FIG. 7 is a diagram showing steps in the method of detecting defects in a substrate according to the invention.

In order to determine these values at each point of the reflected image, a relative displacement of the pattern 3 and the substrate 2 is made along at least one direction in a step 105, so as to displace the fringes 4 of the pattern 3 on the substrate 2, and then in a step 110, displacements of the fringes 4 reflected by the substrate 2 are recorded using the sensor 8, so as to determine the average intensity $I_0$, the contrast $A_0$ and the phase $\phi$ of the image reflected at each point on the image. A sequence of images has to be acquired to be able to determine the average intensity $I_0$, the contrast $A_0$ and the phase $\phi$ of the image reflected at each point on the image. The sequence of images preferably comprises between three and ten images.

Preferably, two sequences of images are acquired, the first sequence of images being acquired using a pattern 3 comprising parallel fringes 4 extending along a first direction, said fringes 4 being displaced orthogonally to the direction of said fringes 4, and the second sequence of images being acquired using a pattern 3 comprising parallel fringes 4 extending along a direction perpendicular to the direction of the fringes 4 in the first sequence of images, said fringes 4 being displaced orthogonally to the direction of said fringes 4.

In one particularly advantageous manner, the image sequence(s) is (are) acquired by projecting a pattern 3 for which the fringes 4 extend parallel and/or perpendicular to a principal crystalline axis of the substrate 2. Said crystalline axis of the substrate may be materialized by a radial notch 9 at the periphery of said substrate 2. it is thus possible to use several sequences of images, each sequence using a pattern 3 for which the fringes 4 are parallel to one of the principal crystalline axes of the substrate 2. Preferably, a sequence of ten images is recorded for each axis. Such an arrangement makes it possible to more efficiently detect slip lines that occur on a monocrystalline substrate, said slip lines that have a length of the order of several hundred microns substantially larger than their width, at the atomic scale, usually being aligned with the crystalline axis of the substrate 2. Thus, one sequence of three images is sufficient to precisely determine the displacements of fringes 4, then the presence and position of defects 10 on the substrate as will be seen later.

The curvature of the surface of the substrate 2 is then determined in a step 115 using the displacements of fringes 4 of the pattern 3. It should be noted that the curvature at each point on the surface of the substrate 2 is calculated by determining the field of local gradients using measurements of the phase of reflected images from displacements of fringes 4 of the pattern 3 then by differentiating said field of local gradients.

The local gradient is the local tangent to the surface, and the curvature is the local radius of curvature.

In step 120, at least one surface defect is detected on the substrate 2 using variations in the curvature of the surface of the substrate 2 calculated above.

Advantageously, this step 120 to detect at least one defect is broken down into a first step 125 to determine points on the surface of the substrate 2 with a radius of curvature greater than or equal to a determined threshold value and/or a local distribution of the curvature statistically different from the distribution of the curvature of the rest of the substrate 2, and a second step 130 to determine the position in space of defects 10 using variations in the gradient and/or curvature of the surface of the substrate 2.

This position in space of defects 10 is determined using a reference point of the substrate 2 as described above. In fact, with reference to FIG. 3, the substrate 2 consists of a flat disk comprising a radial notch 9 forming the reference point, at its periphery.

Accessorily, the method according to the invention may include a step 135 to determine the nature of the detected surface defects obtained by determining amplitude and/or length and/or shape and/or orientation of each surface defect detected in a step 140 and then by comparing the amplitude and/or length and/or shape and/or orientation of each detected surface defect with a database so as to determine the nature of surface defects detected in a step 145.

The relative displacement of the pattern 3 and the substrate 2 may be made along 2 orthogonal directions.

It will be observed that the method according to the invention and the device using said method are particularly suitable for the detection of micro-defects on monocrystalline substrates, particularly by using parallel fringes aligned on the crystalline network of the substrate.

Furthermore, the slip lines thus stand out better than the surface scratches on the substrate 2 that are obviously independent of the crystalline axes of this substrate.

Preferably, the method according to the invention comprises an analysis of the entire surface of the substrate 2 as far as its periphery, in a single sequence of solid wafer type images, particularly at a rate of the order of 100 substrates per hour. Under these conditions, the method according to the invention is capable of obtaining high resolution during detection of shallow defects, in other words defects with a depth of the order of a few nanometers.

Accessorily, it will be noted that the back face of the substrate may also be analysed. To achieve this, the device may comprise a second screen projecting a pattern onto the back face of said substrate and a second sensor, the two faces of said substrate being analysed simultaneously. According to one execution variant, the device may comprise means of turning the substrate over, for example such as a robotized clamp gripping said substrate at its periphery, the two faces of the substrate being then analysed one after the other.

Finally, it is obvious that the examples that have just been given are only particular illustrations and in no way limit application domains of the invention.

The invention claimed is:

1. A method for detecting surface defects, on a substrate designed to be used in electronics, optoelectronics or analogue, the method comprising:
projecting a pattern composed of an alternation of light fringes and dark bands on the substrate, so as to generate fringes reflected by the surface of the substrate;
relatively displacing the pattern and the substrate along at least one direction, so as to displace the fringes of the pattern on the substrate, wherein the fringes of the pattern are parallel to each other and extend parallel to a second principal crystalline axis of the substrate;
acquiring a sequence of at least three images of the pattern reflected by the substrate by a sensor, the images corresponding to displacement of the fringes of the pattern;
determining the gradient of the surface of the substrate using displacements of fringes of the pattern, and
determining the presence of a surface defect on the substrate using variations in the gradient of the surface of the substrate.

2. A method for detecting surface defects, on a substrate designed to be used in electronics, optoelectronics or analogue, the method comprising:
projecting a pattern composed of an alternation of light fringes and dark bands on the substrate, so as to generate fringes reflected by the surface of the substrate;
relatively displacing the pattern and the substrate along at least one direction, so as to displace the fringes of the pattern on the substrate, wherein the fringes of the pattern are parallel to each other and extend parallel to a second principal crystalline axis of the substrate;
acquiring a sequence of at least three images of the pattern reflected by the substrate by a sensor, the images corresponding to displacement of the fringes of the pattern;
determining the gradient of the surface of the substrate using displacements of fringes of the pattern, and
determining the presence of a surface defect on the substrate using variations in the gradient of the surface of the substrate.

3. A method for detecting surface defects, on a substrate designed to be used in electronics, optoelectronics or analogue, the method comprising:
projecting a pattern composed of an alternation of light fringes and dark bands on the substrate, so as to generate fringes reflected by the surface of the substrate;
relatively displacing the pattern and the substrate along at least one direction, so as to displace the fringes of the pattern on the substrate;
acquiring a sequence of at least three images of the pattern reflected by the substrate by a sensor, the images corresponding to displacement of the fringes of the pattern, wherein a first sequence of images is acquired by projecting a pattern for which the fringes are parallel to each other and extend parallel to the principal crystalline axis of the substrate, said fringes being displaced along a direction perpendicular to the direction of the fringes, and a second sequence of images is acquired by projecting a pattern for which the fringes are parallel to each other and extend parallel to the second principal crystalline axis of the substrate, said fringes being displaced orthogonally to the direction of said fringes;
determining the gradient of the surface of the substrate using displacements of fringes of the pattern, and
determining the presence of a surface defect on the substrate using variations in the gradient of the surface of the substrate.

4. The method of claim 1 further comprising determining the position in space of defects determined from variations in the gradient of the surface of the substrate.

5. The method of claim 4, wherein the position in space of the defects is determined by determining the points on the surface of the substrate with a radius of curvature greater than or equal to a given threshold value and/or with a spatial distribution statistically different from the average for the substrate.

6. The method of claim 5, wherein the position in space of defects is determined using a reference point on the substrate.

7. A method for detecting surface defects, on a substrate designed to be used in electronics, optoelectronics or analogue, the method comprising:

projecting a pattern composed of an alternation of light fringes and dark bands on the substrate, so as to generate fringes reflected by the surface of the substrate, wherein the substrate consists of a flat disk comprising a radial notch around its periphery, forming the reference point;

relatively displacing the pattern and the substrate along at least one direction, so as to displace the fringes of the pattern on the substrate;

acquiring a sequence of at least three images of the pattern reflected by the substrate by a sensor, the images corresponding to displacement of the fringes of the pattern;

determining the gradient of the surface of the substrate using displacements of fringes of the pattern;

determining the presence of a surface defect on the substrate using variations in the gradient of the surface of the substrate; and determining the position in space of defects determined from variations in the gradient of the surface of the substrate, wherein the position in space of the defects is determined by determining the points on the surface of the substrate with a radius of curvature greater than or equal to a given threshold value and/or with a spatial distribution statistically different from the average for the substrate.

8. The method of claim 1, further comprising determining the nature of the detected surface defects.

9. The method of claim 8, wherein the nature of surface defects is determined by determining the amplitude and/or the length and/or shape and/or orientation of each detected surface defect.

10. The method of claim 1, wherein the pattern and/or the substrate is moved along two orthogonal directions.

11. A device for the detection of surface defects, on a substrate designed to be used in electronics, optoelectronics or analogue, comprising:

means of projecting a pattern on said substrate composed of an alternation of continuous light fringes and dark bands;

means of introducing relative displacement of the pattern and the substrate along at least one direction, at least one sensor capable of recording displacements of fringes reflected by the substrate;

means of determining the gradient of the surface of the substrate using displacements of the fringes of the pattern;

means of determining the presence of a surface defect on the substrate using variations in the gradient of the substrate surface; and means of generating a laminar flow of a fluid parallel to the surface of the substrate.

12. The device of claim 11, wherein the means of projecting the pattern consist of a screen on which an image is displayed comprising a sequence of light fringes and dark bands.

13. The device of claim 12, wherein the means of relative displacement of the pattern and the substrate consist of an algorithm for processing the video signal transmitted to the screen so as to offset the light fringes and dark bands, the offset being between half a pixel and several pixels, at regular or irregular time intervals, the screen, the substrate and the sensor being fixed.

14. The device of claim 11, wherein the sensor consists of a digital camera comprising a CCD sensor.

15. The device of claim 11, wherein the means of determining the gradient and/or a curvature of the surface of the substrate consist of an algorithm capable of calculating the phase offset of the fringes of the pattern at each point on the surface of the substrate using the signal transmitted by the sensor.

16. The device of claim 15, wherein the means of determining the presence of a surface defect consist of a second algorithm capable of calculating variations in the gradient and/or curvature at each point on the surface of the substrate using phase offsets calculated by the first algorithm.

17. The device of claim 11 further comprising means of determining the position in space of defects on the surface of the substrate.

18. A device for the detection of surface defects, on a substrate designed to be used in electronics, optoelectronics or analogue, comprising:

means of projecting a pattern on said substrate composed of an alternation of continuous light fringes and dark bands;

means of introducing relative displacement of the pattern and the substrate along at least one direction, at least one sensor capable of recording displacements of fringes reflected by the substrate;

means of determining the gradient of the surface of the substrate using displacements of the fringes of the pattern;

means of determining the presence of a surface defect on the substrate using variations in the gradient of the substrate surface; and means of determining the position in space of defects on the surface of the substrate, wherein said means of determining the position in space of defects consist of an algorithm capable of calculating the abscissa and the ordinate of the substrate of each point on the surface of said substrate with a radius of curvature greater than or equal to a determined threshold value and/or with a spatial distribution statistically different from the average of the substrate, relative to a reference point on the substrate.

19. The device of claim 11 further comprising means of supporting said substrate vertically.

* * * * *

UNITED STATES PATENT AND TRADEMARK OFFICE
CERTIFICATE OF CORRECTION

| | |
|---|---|
| PATENT NO. | : 7,812,942 B2 |
| APPLICATION NO. | : 12/057367 |
| DATED | : October 12, 2010 |
| INVENTOR(S) | : Cecile Moulin et al. |

It is certified that error appears in the above-identified patent and that said Letters Patent is hereby corrected as shown below:

- In claim 1, column 10, line 2, "second" has been changed to "first".

- In claim 7, column 11, line 8, "the reference point" has been changed to "a reference point".

Signed and Sealed this
First Day of February, 2011

David J. Kappos
*Director of the United States Patent and Trademark Office*